United States Patent
Sindel et al.

(10) Patent No.: US 6,416,038 B1
(45) Date of Patent: Jul. 9, 2002

(54) INLINE PROCESS VALVE ASSEMBLY

(75) Inventors: Loyd C. Sindel, Byron; Walter L. Connolly, Moraga; Luther Thomas Hoobyar, Mountain View, all of CA (US)

(73) Assignee: Aseptic Controls Investment Co., San Francisco, CA (US)

( * ) Notice: Subject to any disclaimer, the term of this patent is extended or adjusted under 35 U.S.C. 154(b) by 0 days.

(21) Appl. No.: 09/642,608

(22) Filed: Aug. 17, 2000

(51) Int. Cl.⁷ .................................................. F16K 1/02
(52) U.S. Cl. ..................................... 251/331; 251/335.2
(58) Field of Search ................................ 251/331, 335.2

(56) References Cited

U.S. PATENT DOCUMENTS

| | | | |
|---|---|---|---|
| 2,705,124 A | * 3/1955 | Price et al. ............. 251/331 X |
| 2,963,266 A | * 12/1960 | Boteler ....................... 251/331 |
| 2,988,322 A | * 6/1961 | Anderson .................... 251/331 |
| 3,020,020 A | * 2/1962 | Boetler ....................... 251/331 |
| 3,091,427 A | * 5/1963 | Boteler ................... 251/331 X |
| 3,103,342 A | * 9/1963 | Boteler ....................... 251/331 |
| 3,298,660 A | * 1/1967 | Price et al. ................. 251/331 |
| 4,029,296 A | * 6/1977 | Hartmann et al. .......... 251/331 |
| 4,072,292 A | * 2/1978 | Banon ........................ 251/331 |
| 4,319,737 A | * 3/1982 | Waterfield .................. 251/331 |
| 5,152,500 A | 10/1992 | Hoobyar et al. ............ 251/269 |
| 5,452,746 A | 9/1995 | Hoobyar et al. ............ 137/886 |

FOREIGN PATENT DOCUMENTS

FR           1211043        * 3/1960    ................. 251/331

* cited by examiner

Primary Examiner—James Hook
Assistant Examiner—John Bastianelli
(74) Attorney, Agent, or Firm—Flehr Hohbach Test Albritton & Herbert LLP

(57) ABSTRACT

An inline process valve assembly having a valve body of a rigid material having a thru bore which is circular in cross-section forming a flow passage extending through the valve body along a longitudinal axis and having a lower arcuate surface. A cone-shaped recess is formed in the body and has a central vertical axis extending perpendicular to the longitudinal axis. The cone-shaped recess opens into the flow passage and has an hemispherical rounded nose which is generally coincident with the lower arcuate surface of the flow passage. A cone-shaped diaphragm of a flexible material disposed in said cone-shaped recess and is movable between open and closed positions with respect to the flow passage. The diaphragm has an outer margin. A clamp is provided for clamping the outer margin of the diaphragm to the valve body to form a liquid-tight and air-tight seal between the diaphragm and the body. An operator is secured to the diaphragm for moving the diaphragm between said open and closed positions.

8 Claims, 3 Drawing Sheets

INLINE PROCESS VALVE ASSEMBLY

This invention relates to an inline process valve assembly.

Inline process valves have heretofore been provided. Such inline process valves have been found to be objectionable because often they were found to be sources of contamination due to entrapped material. They have been difficult to assemble, disassemble and clean. Such valves have utilized a flat plate diaphragm which presses down on a weir to interrupt the flow in the middle of the body of the valve. With such a valve it has been found difficult to obtain consistent seals. There is therefore a need for a new and improved inline process valve and assembly thereof.

In general, it is an object of the present invention to provide an inline process valve in which positive consistent seals, can be obtained while withstanding normal operating pressures of flow liquids.

Another object of the invention is to provide a valve of the above character in which there is no trapped material.

Another object of the invention is to provide a valve of the above character in which there is a straight through flow through the inline valve.

Another object of the invention is to provide a valve of the above character which can be easily cleaned.

Another object of the invention is to provide a valve of the above character which can be readily assembled and disassembled.

Another object of the invention is to provide a valve of the above character which can be readily maintained.

Another object of the invention is to provide a valve of the above character which can be economically produced.

Additional objects and features of the invention will appear from the following description in which the preferred embodiments are set forth in detail in conjunction with the accompanying drawings.

Figure 1:
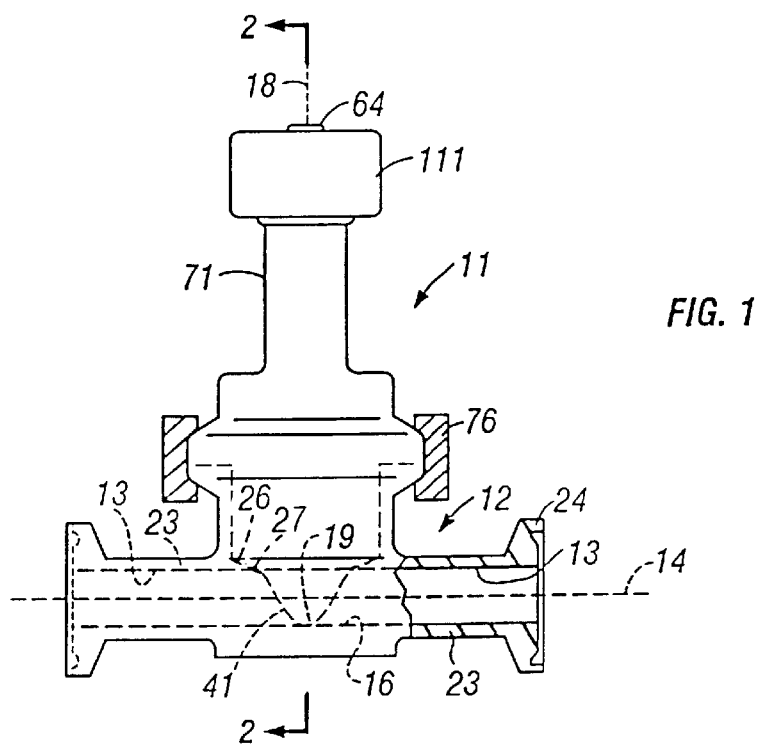
FIG. 1 is a side elevational view of an inline process valve assembly incorporating the present invention with certain portions broken away.

In general, the inline process valve assembly of the present invention comprises a valve body of a rigid material having a through bore which is circular in cross section and forms a flow passage extending along a longitudinal axis.

The through bore has a lower arcuate surface. A cone-shaped recess is formed in the body and has a central vertical axis extending perpendicular to the longitudinal axis. The cone-shaped recess opens into the flow passage and has a hemispherical rounded apex which is generally coincident with the lower arcuate surface of the flow passage. An annular shoulder is formed in the body and has an inclined lip adjacent the flow passage and circumscribing the cone-shaped recess. A cone-shaped diaphragm of a flexible material is disposed in the cone-shaped recess and is movable between open and closed positions with respect to the flow passage. The cone-shaped diaphragm in a closed position forms a seal with the lip and a continuous seal throughout the conical surface of the diaphragm. The cone-shaped diaphragm has an outer margin. A clamp is provided for clamping the outer margin of the diaphragm to the shoulder of the body to form a liquid-tight seal. Operator means is secured to the diaphragm for moving the diaphragm between the open and closed positions.

More in particular, the inline process valve assembly 11 of the present invention consists of a valve body 12 which is formed of a suitable material which can be utilized for aseptic processes. One material found to be particularly satisfactory is 316L stainless which is a low carbon stainless which is suitable for welding. In the present invention where an integral body is provided with which no welding is necessary, weldable material need not necessarily be used. However, for special adaptations of the valve assembly 11, additional ports may be desired and can be added by welding. For such cases 316L should be used for the valve body 12. The valve body 12 of the present invention is made from machined bar stock and which has an outer surface which is generally cylindrical. The valve body 12 is provided with a through or thru-bore 13 which is circular in cross section and is free of discontinuities that forms a flow passage extending through the valve body 12 along a longitudinal axis 14. The thru-bore 13 has a lower arcuate surface 16 which is utilized for making a seal as hereinafter described.

Figure 3:
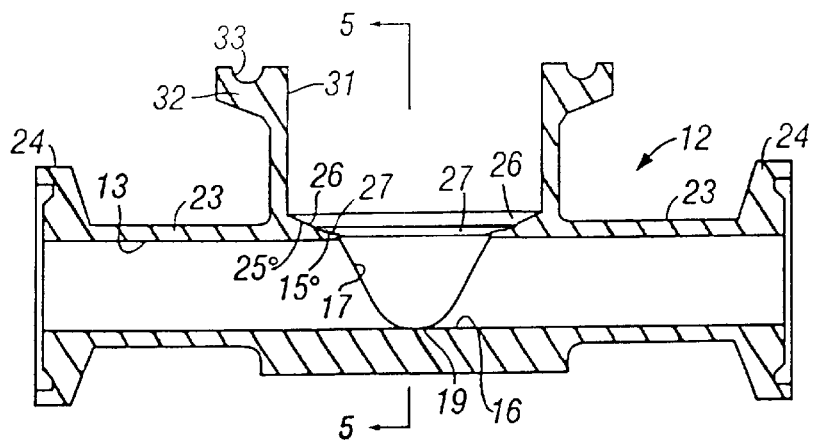
FIG. 3 is an enlarged cross sectional view of the valve body shown in FIG. 1.
Figure 2:
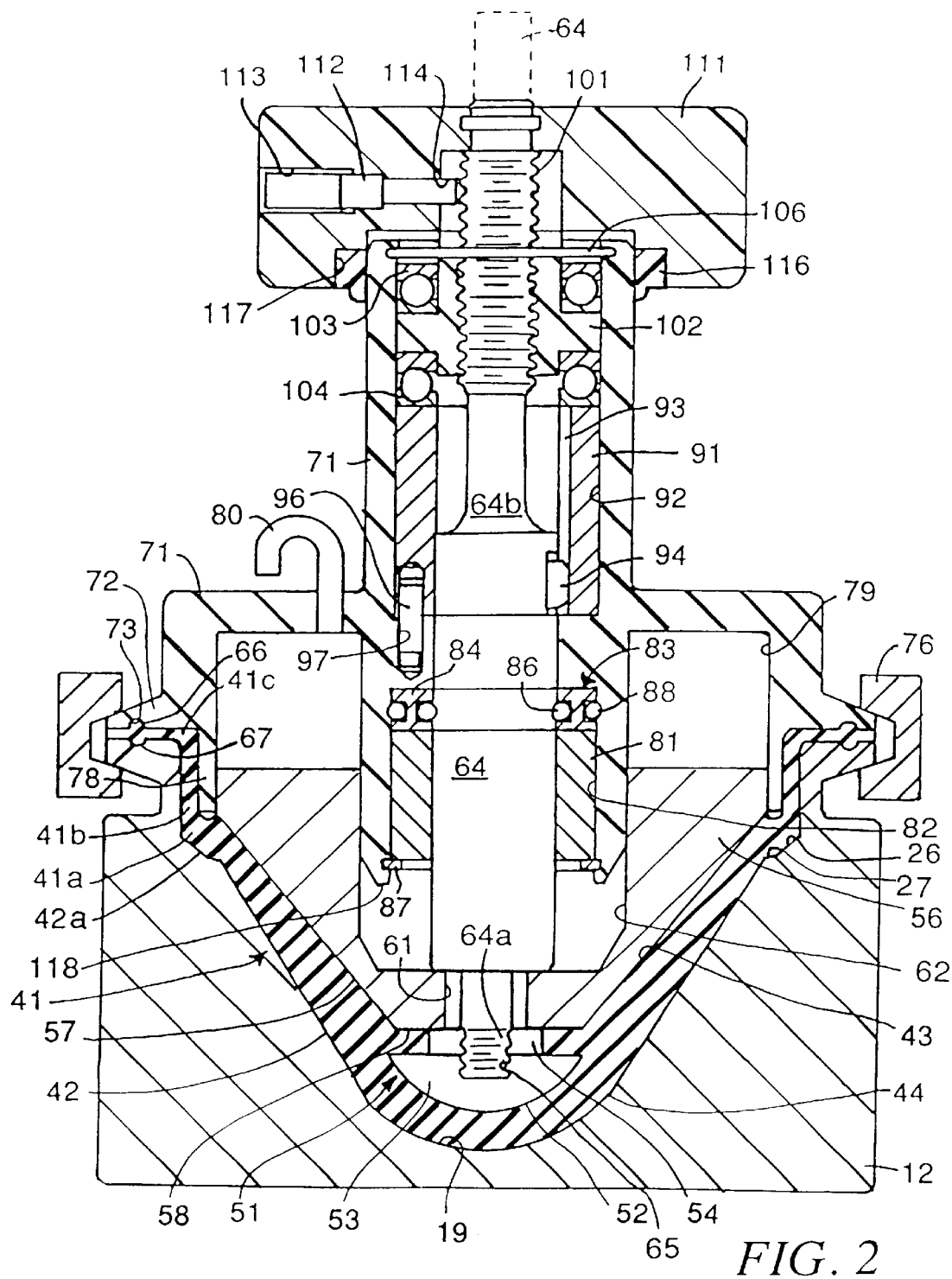
FIG. 2 is an enlarged cross sectional view taken along the line 2—2 of FIG. 1.
Figure 5:
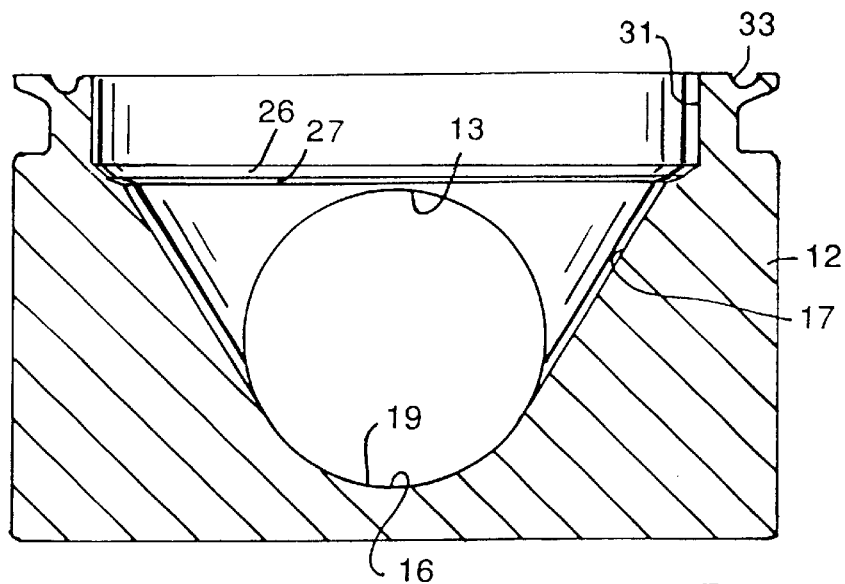
FIG. 5 is a cross sectional view taken along the line 5—5 of FIG. 3.
Figure 6:
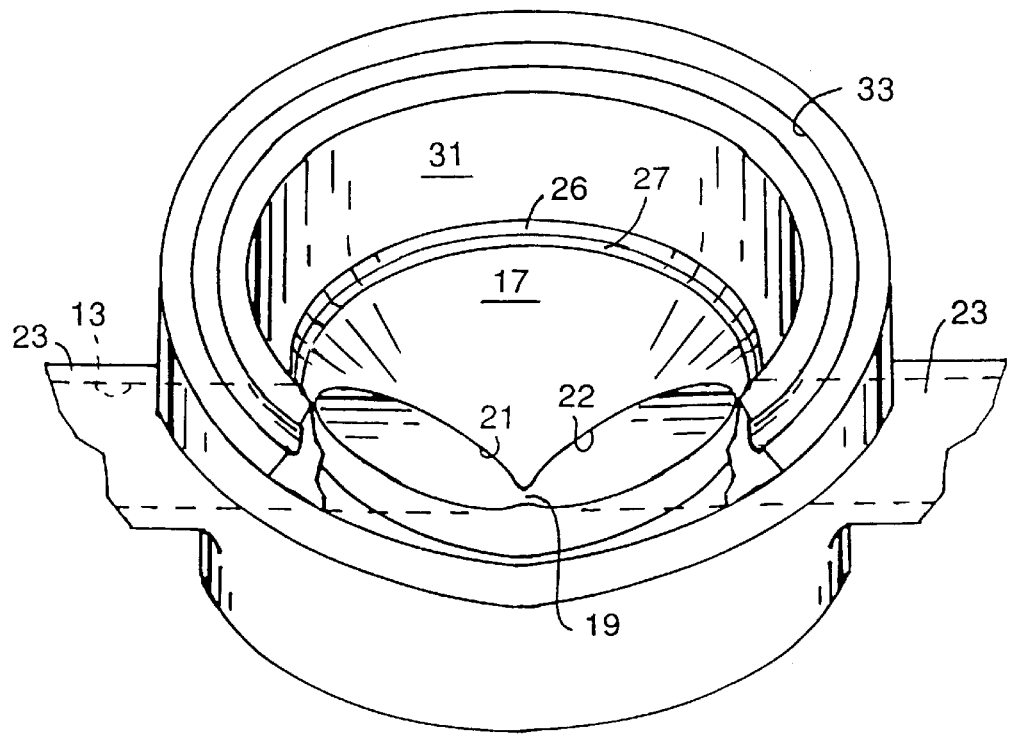
FIG. 6 is an isometric angle view of the valve body shown in FIG. 3 with certain portions broken away.

A cone-shaped recess or hole 17 (see FIG. 3) is formed in the body 12 extending down into the body to the lower arcuate surface 16 along a central vertical axis 18 perpendicular to the longitudinal axis 14. The cone-shaped recess 17 opens into the flow passage provided by the thru-bore 13 and terminates in a hemispherical rounded nose or apex 19 which is coincident with the lower arcuate surface 16 of the flow passage formed by the thru-bore 13. In order to ensure that there is no degradation of the thru bore, the nose or hemispherical apex 19 of the cone-shaped recess 17 is displaced upwardly by 0.002". This eliminates any scoring of the thru bore during machining of the cone-shaped recess 17 into the valve body 12. The thru-bore 13 extending through the cone-shaped recess 17 forms oval-shaped openings 21 and 22 on opposite sides of the conical or cone-shaped recess 17 (see FIG. 6).

The valve body 12 is provided with extensions 23 on opposite ends of the same of a reduced diameter through which the thru-bore 13 extends. Ferrules 24 of a conventional type are provided on the outer ends of the extensions 23 and are adapted to be clamped by a conventional means to piping by conventional clamps (not shown).

Figure 4:
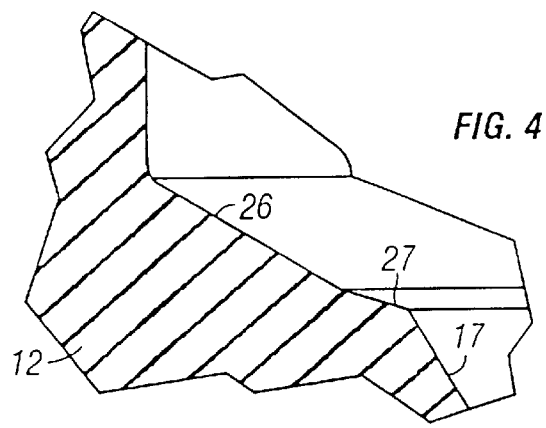
FIG. 4 is an illustration showing a lip detail of the valve body shown in FIG. 2.

The valve body 12 is provided with an annular sealing surface in which at least a portion thereof is planar in the form of an annular major planar shoulder 26 (see FIG. 3) which has an annular inwardly extending lip 27 which is immediately adjacent the cone-shaped recess 17 and from which the cone-shaped recess extends downwardly. A detail review of the shoulder 26 and the lip 27 is shown in FIG. 4. As shown therein, the shoulder 26 extends at a suitable angle from the horizontal as for example 25° whereas the lip 27 extends at an angle from the horizontal of 15° with respect to the longitudinal axis of the thru-bore 13. A tangent line projected from the radius of the rounded nose or apex 19 to the inner edge of the lip 27 provides the angle for the surface of the cone-shaped recess 17. Thus as shown in FIG. 4, the conical recess 17 extends at an angle as for example 41.28° for a ½" valve and 58.44° for a 2" valve with reference to the longitudinal axis of the thru-bore 13. The upper edge of the cone-shaped recess 17 is coincident with the inner edge of the lip 27.

By way of example for a ½" inline valve body, the nose 19 can have a radius of 0.185", the shoulder 26 can have a length along the horizontal of 0.164", whereas the lip 27 can have a length along the horizontal of 0.031". The transition between the slope of the conical surface 17 and the slope of the lip 27 can be radiused an appropriate amount as for example a 0.005" radius. The lip 27 can have a dimension in the vertical direction of 0.009" whereas the shoulder 26 can have a dimension in the vertical direction of 0.076". The outer extremity of the shoulder 26 extends to a cylindrical recess 31 of a suitable dimension as for example 1.397". The recess 31 extends upwardly through a ferrule in the form of an integral flange 32 that is provided with an upwardly facing annular recess 33.

A cone-shaped diaphragm 41 is disposed in the cone-shaped recess 17. It is dimensioned so that it can form a close fit with the cone-shaped recess 17. The cone-shaped diaphragm 41 is formed of a suitable flexible material such as a medical grade plastic or rubber. The diaphragm 41 is provided with an outer conical surface 42 that has a conformation which generally conforms to the conformation of the cone-shaped recess 17. It is also provided with an inner conical surface 43 which is inclined at a lesser angle than the outer conical surface 42 so as to provide an increasing wall thickness for the diaphragm 41 in a downwardly extending direction towards a hemispherical nose 44.

It has been found that this increased thickness is desirable in order to prevent wrinkling of the outer conical surface 42 during and after moving the diaphragm between a closed to an open position as hereinafter described. Thus by way of example, the thickness of the material has been increased from ⅛" to about ³⁄₁₆–⁵⁄₁₆". This provides a greater stiffness to the diaphragm to prevent wrinkling or folding of the diaphragm. Typically the radius of the nose is the radius of the thru bore 13 as for example 0.935" for a 2" valve.

By way of example the exterior outer conical surface 42 at an outwardly extending portion 42a can have a suitable slope as for example 28°. This ensures that there will be an initial contact with the annular lip 27 having the 15° slope. Making an initial contact at this location adjacent where the cone-shaped recess 17 enters the thru-bore 13 ensures that there is no cavity facing inwardly from that lip. In ascertaining the slope, it is desirable that there be a 3° change in the slope with reference to the 25° major shoulder 26 to ensure this initial contact. However, the difference in slope can range from 2–4°.

A rigid metal insert 51 is molded into the nose 44 of the diaphragm 41. This insert 51 has a lower hemispherical surface 52 provided by a hemispherical head 53 embedded in the rubber diaphragm 41 and is utilized to provide forces which are uniformly distributed over the hemispherical nose 44 to squeeze the rubber diaphragm uniformly against the bottom or lower arcuate surface 16 of the thru-bore 13. The insert 51 is also provided with a shoulder 54 of a smaller diameter than the largest diameter of the head 53 and extends upwardly into engagement with a squeeze cup 56.

The squeeze cup 56 is formed of a suitable rigid material such as aluminum and is disposed within the conical recess formed by the inner conical surface 43 in the diaphragm 41. It is provided with a conical surface 57 which generally corresponds in size and angularity to the inner conical surface 43. The squeeze cup 56 has a lower planar surface 58 which engages the shoulder 54 of the insert 51. The squeeze cup 56 is provided with a bore 61. The squeeze cup 56 is also provided with a cylindrical recess 62 of a substantially larger diameter than the bore 61 that receives an operating stem 64. The operating stem 64 is provided with an integral threaded extension 64a extending through bore 61 and is threaded into a threaded bore 65 in the insert 51 to form a secure threaded connection between the insert 51, the stem 64 and the squeeze cup 56 and at the same time securing the squeeze cup 56 within the diaphragm 41. When forces are applied to the operating stem 64 as hereinafter described, the forces are applied to the rigid squeeze cup 56 which equitably distributes forces over the inner conical surface 43 and in turn causes equal distribution of squeeze forces to the outer conical surface 42 of the diaphragm 41 to provide uniform sealing pressures as hereinafter described.

The diaphragm 41 is provided with a portion 41a of increased thickness in the vicinity of the shoulder 26 and the lip 27 to ensure making a good seal therewith as hereinafter described. It is also provided with an upwardly extending portion 41b and a horizontally extending portion 41c. The horizontally extending portion 41c is provided with upper and lower toroidal portions 66 and 67 formed integral therewith. The toroidal portion 67 is adapted to seat in the annular recess 33.

Means is provided for forming a sealing engagement between the portion 41c of the diaphragm 41 and the ferrule or integral flange 32 and a cylindrical sleeve 71 that is provided with an outwardly extending flange 72 having formed therein a downwardly facing semicircular recess 73 which is adapted to receive and fit over the toroidal portion 66 of the portion 41c of the diaphragm 41. A clamp 76 of a conventional type secures the flange 72 to the ferrule or integral flange 32 to form an air-tight and liquid-tight seal between the valve body 12 and the diaphragm 41. The sleeve 71 is provided with an annular downwardly extending tongue 78 that engages the portion 41a of the diaphragm and serves to firmly clamp the portion 41a to the annular shoulder 26 and the annular lip 27 by providing localized positive clamping on the diaphragm in this annular region. The sleeve 71 is also provided with a cylindrical recess 79 which receives the upper extremity of the squeeze cup 56. This recess 79 is vented to the atmosphere through a vent pipe 80.

As shown, the operating stem 64 extends upwardly through the sleeve 71. The operating stem is mounted in a bushing 81 provided in a cylindrical recess 82 in the sleeve 71. The upper end of the bushing 81 engages an upper sealing assembly 83 comprising a seal ring 84 which carries inner and outer o-ring seals 86 and 88. A retaining ring 87 engages the lower extremity of the bushing 81 and holds it in place.

A key sleeve 91 is disposed in a cylindrical recess 92 provided in the sleeve 71. The key sleeve 91 is provided with a keyway 93 extending longitudinally thereof and which slidably receives a key 94 fitted into the stem 64. A pin 96 is provided which is secured by a press fit into the lower extremity of the key sleeve 91 and is seated within a hole 97 in the sleeve 71 that serves to prevent rotation of the key sleeve 91 with respect to the sleeve 71.

The stem 64 is provided with a portion 64b of reduced diameter in which acme threads 101 are provided on the upper extremity. A stem nut 102 is seated within the sleeve 71 between upper and lower thrust bearing assemblies 103 and 104. The bearing assemblies 103 and 104 and the stem nut 102 are retained in place by a snap ring 106.

A knob 111 adapted to be operated by the human hand is secured to the stem nut 102 by a set screw 112. The set screw 112 extends through a hole 113 in the knob 111 and through a hole 114 in the stem nut 102 to positively and frictionally engage the acme threads 101 to ensure positive engagement. An annular wiper 116 of a resilient material is provided in an annular recess 117 opening downwardly through the bottom surface of the knob immediately adjacent the sleeve 71 and engages the sleeve 71 to prevent washdown water, dirt and exterior contamination from entering into the valve assembly 11.

As can be seen, the stem 64 is adapted to project through the knob 111. When the valve is in the closed position, the stem 64 extends outwardly nearly flush with the top surface of the valve. When the valve is opened, the stem sticks out by the full amount of travel of the stem 64 in moving toward the open position.

Operation and use of the inline process valve assembly 11 may now be briefly described as follows. Let it be assumed that the inline valve is installed in a piping installation in a pharmaceutical plant. Let it also be assumed that the valve assembly 11 is in a closed position and that there is now a need for a demand for fluid flow downstream. To open the valve assembly, the operator grasps the knob 111 and rotates the knob in a counterclockwise direction. The operator can determine the amount of opening by observing the length of the stem 64 protruding above the knob. If necessary and desired, the operator can operate the knob 111 until it is in a fully open position in which case the bottom of the bore 62 of the squeeze cup 56 will hit the end of the sleeve 71 at point 118. Thus, the squeeze cup serves as a physical stop to prevent further rotation of the knob 111. During opening of the valve, there is a realignment of the rubber forming the diaphragm 41. The diaphragm 41 continues to bridge the cavity between the conical surface of the squeeze cup 56 and the guide section of the sleeve which surrounds the squeeze cup. In connection with the present invention it has been found that with full opening of the valve assembly 11 there is no overlapping visible on the exterior conical surface of the diaphragm or in other words on the product flow side of the diaphragm to thus assure cleanability.

Even when the valve is in a completely open position, a seal is continued to be formed between the portion 41a and the shoulder 26 and the annular lip 27. The seal is not disturbed because the portion 41a is held in place by the depending tongue 78. Any flexing of the diaphragm 41 is forced to occur inwardly from the lip 27. When the valve assembly of the present invention is in this open position, there is substantially unimpeded flow through the flow passage formed by the thru-bore 13 because only a small portion of the lower extremity of the conical diaphragm 41 extends into the flow passage.

Now let it be assumed that it is desired to close the valve assembly 11 from its open position. To do this, the operator rotates the knob 111 in a clockwise or opposite direction which will move the stem 64 and the diaphragm 41 downwardly so that the outer conical rubber surface of the diaphragm is brought into contact with the oval-shaped openings 21 and 22 and the bottom of the thru-bore 13. As hereinbefore pointed out, the squeeze cup 56 in conjunction with the insert 51 causes substantially uniform distributed closing forces to be applied by the conical surface of the diaphragm 41 to the corresponding conical surface formed by the cone-shaped recess 17 in the valve body 12. In this way, an effective seal is created around each oval-shaped opening 21 and 22 which when the valve assembly 11 is closed before flow begins prevents the liquid flowing through the piping from coming into the conical area of the valve body cavity. Thus each end of the thru-bore 13 entering the conical cavity is sealed. At the same time another continuous seal is formed around the annular shoulder 26 and annular lip 27. As pointed out previously, the raised lip 27 produces localized sealing against the rubber diaphragm 41 and assures that there is a primary seal at the innermost extremity of the inner lip, thereby preventing any liquid product from entering the outer margins of the shoulder seal.

This engagement of the cone-shaped diaphragm with the surfaces can be readily felt by the operator when at least some resistance in rotation of the knob 111 occurs. Thereafter, the operator to ensure that there is a good seal need only rotate the knob 111 with an appropriate torque as for example 75 inch pounds.

Because of the conical shape of the diaphragm, there is no flattening of the diaphragm by repeated opening and closing of the valve. With the valve of the present invention it has been found that viable repeated sealing can be obtained during closing of the valve. There is no leakage and there is no possibility of contamination because there is no possibility of entrapping product within the valve. The valve has a construction which can be easily maintained and cleaned. It also is a construction which can be readily and economically manufactured. Although the valve assembly 11 has been described for use with a manual operator, it should be appreciated that it can be operated automatically such as by a pneumatically controlled operator.

What is claimed:

1. An inline process valve assembly comprising a valve body of a rigid material having a thru bore which is circular in cross-section free of discontinuities forming a flow passage extending through the valve body along a longitudinal axis and having a lower arcuate surface, a cone-shaped recess formed in the body and having a central vertical axis extending perpendicular to the longitudinal axis, said cone-shaped recess opening into the flow passage and having a hemispherical rounded nose which is generally coincident with the lower arcuate surface of the flow passage, said body having an annular planar sealing surface immediately adjacent the cone-shaped recess, said annular planar sealing surface including an annular inclined planar shoulder and an inclined annular lip, said inclined annular lip being inclined at a lesser angle with respect to the longitudinal axis than the inclined annular shoulder, a cone-shaped diaphragm of a flexible material disposed in said cone-shaped recess and movable between open and closed positions with respect to said flow passage, said diaphragm having an outer margin and means for clamping the outer margin of the diaphragm to the valve body to form a liquid-tight and air-tight seal between the diaphragm and the body, said diaphragm having a portion thereof engaging the sealing surface prior to making contact with the cone-shaped recess in movement toward the closed position and operator means secured to the diaphragm for moving the diaphragm between said open and closed positions.

2. A valve assembly as in claim 1 wherein said means for clamping the outer margin of the diaphragm to the valve body includes a depending annular tongue engaging said portion of the diaphragm engaging the sealing surface.

3. A valve assembly as in claim 1 wherein said thru bore opens into said conical recess to form oval-shaped openings on opposite sides of the conical recess and wherein said diaphragm in the closed position forms a seal with respect the oval-shaped openings and the lower arcuate surface of the flow passage.

4. A valve assembly as in claim 3 wherein said diaphragm forms seals all the way around said oval-shaped openings.

5. A valve assembly as in claim 1 wherein said diaphragm has a hemispherical nose portion for engaging the lower arcuate portion of the thru bore.

6. A valve assembly as in claim 1 wherein said diaphragm is provided with an inner conical surface, said inner conical surface being inclined at an angle less than that of the outer inclined surface to provide a wall thickness for the diaphragm which increases in a direction towards the hemispherical nose.

7. A valve assembly as in claim 6 further including a rigid insert molded into the hemispherical nose portion of the diaphragm, said insert having a curved outer surface generally corresponding to the curvature of the nose portion of the diaphragm whereby when dosing pressure is applied to the diaphragm, the squeeze forces are uniformly supplied to the nose portion through the insert.

8. A valve assembly as in claim 7 further including a squeeze cup formed of a rigid material disposed within the diaphragm and having an outer surface corresponding generally to the inner surface of the diaphragm whereby when forces are applied to the squeeze cup, the squeeze forces are substantially uniformly distributed over the conical surface of the diaphragm.

* * * * *